United States Patent
Allen et al.

(10) Patent No.: US 7,282,317 B2
(45) Date of Patent: Oct. 16, 2007

(54) DYE COMPLEXES AND USE THEREOF IN IMAGING MEMBERS AND METHODS

(75) Inventors: Richard M. Allen, Norton, MA (US); Michael P. Filosa, Medfield, MA (US); Stephen J. Telfer, Arlington, MA (US)

(73) Assignee: Zink Imaging, LLC, Waltham, MA (US)

( * ) Notice: Subject to any disclaimer, the term of this patent is extended or adjusted under 35 U.S.C. 154(b) by 373 days.

(21) Appl. No.: 10/789,600

(22) Filed: Feb. 27, 2004

(65) Prior Publication Data

US 2004/0171817 A1 Sep. 2, 2004

Related U.S. Application Data

(60) Provisional application No. 60/451,208, filed on Feb. 28, 2003.

(51) Int. Cl.
*G03F 7/00* (2006.01)
*G03F 7/004* (2006.01)

(52) U.S. Cl. .................... 430/270.1; 430/330
(58) Field of Classification Search ............. 430/330, 430/270.1
See application file for complete search history.

(56) References Cited

U.S. PATENT DOCUMENTS

| | | | |
|---|---|---|---|
| 4,097,288 A | 6/1978 | Lawton | 106/21 |
| 4,232,552 A | 11/1980 | Hof et al. | 73/356 |
| 5,177,262 A | 1/1993 | Taylor et al. | 564/156 |
| 5,338,644 A | 8/1994 | Taylor et al. | 430/214 |
| 6,054,246 A | 4/2000 | Bhatt et al. | 430/151 |
| 6,537,410 B2 | 3/2003 | Arnost et al. | 156/235 |

FOREIGN PATENT DOCUMENTS

| | | |
|---|---|---|
| GB | 1 298 462 | 12/1972 |
| JP | 59062666 | 4/1984 |
| JP | 62288828 A * | 12/1987 |
| JP | 07076587 | 3/1995 |

OTHER PUBLICATIONS

English language abstract of JP 62-288828 A.*
Savvin et al, "Mechansim of action of cationic surfactants in Organic reagent-metal ion-surfactant systems", pp. 1473-1480. (1978), 33(8).*
U.S. Appl. No. 10/789,648, filed Feb. 27, 2004, Chu et al.
U.S. Appl. No. 10/789,566, filed Feb. 27, 2004, Cheon et al.
U.S. Appl. No. 10/789,276, filed Feb. 27, 2004, Cheon et al.
U.S. Appl. No. 10/151,432, filed May 20, 2002, Bhatt et al.
"Equilibria of bisphenol complexation with pyridine in acetonitrile solutions", Zhurnal Obshchei Khimii (1993), pp. 1869-1871 by Titov et al. Journal written in Russian. English Abstract.
"Hydrogen-bonding-based thermochromic phenol-amine complexes", Journal of Physical Organic Chemistry, vol. 11, pp. 737-742 (1998) by Mizutani et al.
"Hydrogen Bond Equilibria of Phenol-Pyridine in Cyclohexane $CCl_4$, and Benzene Solvents", J. Phys. Chem. (1987), pp. 1673-1674 by Spencer et al.
"Formation of Hydrogen-bonded Complexes between Phenol and Some Heterocyclic Bases in Carbon Tetrachloride", J. Chem. Soc. Perkin Trans. II (1987), pp. 1815-1817, by Orban et al.
"Infrared study of the interaction between proton donors and 1,10-phenanthroline derivatives", Spectrochimica Acta, vol. 45A, (1989) pp. 1297-1304 by Siegel et al.

* cited by examiner

*Primary Examiner*—Amanda Walke
(74) *Attorney, Agent, or Firm*—Michel Morency; James F. Ewing; Foley & Lardner LLP

(57) ABSTRACT

There are described novel complexes formed between hydrogen bond acceptors and phenolic dye compounds and imaging members and imaging methods, including thermal imaging members and methods utilizing the complexes.

5 Claims, No Drawings

DYE COMPLEXES AND USE THEREOF IN IMAGING MEMBERS AND METHODS

REFERENCE TO RELATED APPLICATIONS

This application claims the benefit of provisional application Ser. No. 60/451,208, filed Feb. 28, 2003.

This application is related to the following commonly assigned United States patent applications and patents, the disclosures of all of which are hereby incorporated by reference herein in their entirety:

U.S. patent application Ser. No. 10/789,648, filed on even date herewith;

U.S. patent application Ser. No. 10/789,566, filed on even date herewith;

U.S. patent application Ser. No. 10/789,276, filed on even date herewith;

U.S. Pat. No. 6,537,410 B2;

U.S. patent application Ser. No. 10/151,432 filed May 20, 2002; and

U.S. Pat. No. 6,054,246.

FIELD OF THE INVENTION

This invention relates to novel compounds and, more particularly, to compounds which exhibit one color in the crystalline form and a second, different color in the liquid, or amorphous, form. Also described are imaging members and imaging methods, including thermal imaging members and methods, which utilize such dyes.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be as higher than the lamination temperature by as small a margin as possible, as would be the case for time-independent temperature of coloration.

Finally, the imaging system may comprise more than one color-forming layer and be designed to be printed with a single thermal print-head, as described in the above-mentioned patent application Ser. No. 10/151,432. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204-5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274-275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

As the state of the art in imaging systems advances and efforts are made to provide new imaging systems that can meet new performance requirements, and to reduce or eliminate some of the undesirable characteristics of the known systems, it would be advantageous to have new dye compounds which can be used in imaging systems, including thermal imaging systems.

SUMMARY OF THE INVENTION

It is therefore an object of this invention to provide novel compounds.

Another object of the invention is to provide novel compounds which exhibit different colors when in the crystalline form and in the liquid form.

Yet another object of the invention is to provide imaging members and methods, including thermal imaging members and methods, which utilize the novel compounds.

The present invention provides novel compounds which include a dye moiety and a radical of a complexing agent. The novel compounds are useful as image dyes in thermal imaging systems. According to one aspect of the invention there are provided novel compounds which exhibit a first color when in the crystalline form and a second color, different from the first color, when in the liquid, amorphous form.

In one embodiment of the invention there are provided novel compounds which are represented by formula I:

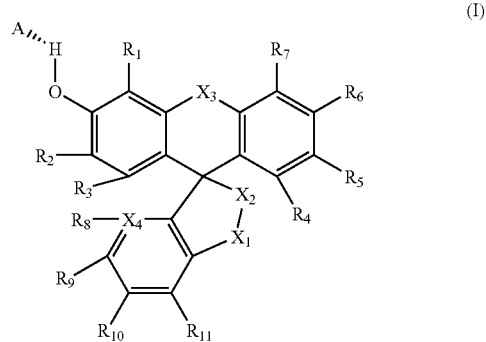

(I)

wherein:

$R_1$, $R_2$, $R_3$, $R_4$, $R_5$, and $R_7$ are each independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_6$ is selected from the group consisting of halogen, oxygen, substituted oxygen, nitrogen, substituted nitrogen, sulfur and substituted sulfur;

$R_8$, $R_9$, $R_{10}$ and $R_{11}$ are each independently absent or selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$X_1$ is selected from the group consisting of carbonyl, methylene, substituted methylene and sulfonyl;

$X_2$ is selected from the group consisting of oxygen, nitrogen and substituted nitrogen;

$X_3$ is selected from the group consisting of oxygen, sulfur, nitrogen and substituted nitrogen; and $X_4$ is carbon or nitrogen.

The radical A of the complexing agent can be any hydrogen-bond acceptor which forms a hydrogen bond with a phenolic group. The complexing agent and the dye form a crystalline complex in which the dye is associated with the complexing agent. The molar ratio of dye to complexing agent may be greater than 1:1 when the complexing agent comprises more than one hydrogen bond accepting radical, or less than 1:1 when more than one of the substituents on the dye is a hydrogen bond donor. Particularly effective complexing agents are weakly basic heterocyclic amines such as pyridines, phenanthrolines and pyrazines, which can be represented by formula II:

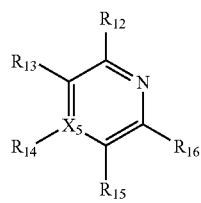

(II)

wherein $R_{12}$, $R_{13}$, $R_{14}$, $R_{15}$ and $R_{16}$ can each independently be hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, substituted oxygen, nitrogen, substituted nitrogen, substituted sulfur; and $X_5$ can be carbon or nitrogen.

Specific preferred examples of this class of complexing agents are phenanthroline, 2,9-dimethylphenanthroline, 4,5,6,7-tetramethylphenanthroline, methyl picolinate, ethyl picolinate, pyrazine, 4,4'-bipyridine, 2,2'-bipyridine, 1,2-bis(4-pyridyl)ethane and trans-1,2-bis(4-pyridyl)ethylene.

The hydrogen bond acceptor A can also be a substituted imidazole or benzimidazole as represented by formula III

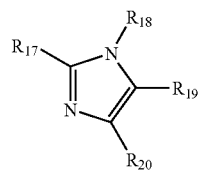

(III)

wherein $R_{17}$, $R_{19}$ and $R_{20}$ can each independently be hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, substituted oxygen, nitrogen, substituted nitrogen, or substituted sulfur; and $R_{18}$ can be alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, sulfonyl, aryl, substituted aryl, heteroaryl, substituted heteroaryl, substituted oxygen or substituted nitrogen.

Specific preferred examples in this class are 1-benzylimidazole, 1-benzyl-2-phenylimidazole, 1-benzyl-2-methylimidazole, 1-benzylbenzimidazole, 1-benzyl-2-methybenzimidazole, 1-(2-ethoxy-1-ethyl)benzimidazole, 1-(2-methoxy-1-ethyl)-2-methylbenzimidazole, 1-ethyl-2-phenylbenzimidazole, and 1-benzyl-2-(4-chlorophenyl)benzimidazole.

Another class of effective complexing agents are amides. The amide complexing agents are represented by formula IV

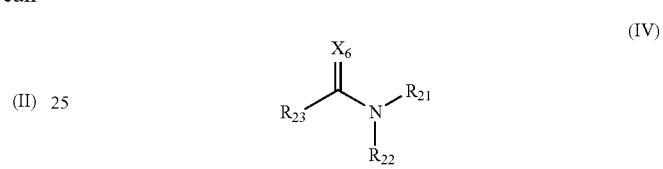

(IV)

wherein:

$R_{21}$ and $R_{22}$ can each be independently alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, sulfonyl, aryl, substituted aryl, heteroaryl or substituted heteroaryl, or $R_{21}$ and $R_{22}$ taken together with the nitrogen atom to which they are attached can form a heterocycloalkyl ring having four to eight members, $R_{23}$ can be alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, sulfonyl, aryl, substituted aryl, heteroaryl, substituted heteroaryl, substituted oxygen, substituted nitrogen or substituted sulfur, or $R_{22}$ and $R_{23}$ taken together with the nitrogen and carbon atoms to which they are respectively attached can form a heterocycloalkyl ring having four to eight members; and $X_6$ can be oxygen, sulfur or substituted nitrogen.

Specific preferred examples of this class are terephthalamides such as N,N,N',N'-tetramethylterephalamide and the corresponding tetrabutyl derivative, cyclic oxalamides such as 1,4-dimethyl-2,3-dioxopiperazine, dimethylbenzamide, N-acetylindoline, N-propionylindoline, N-acetyl-5-bromoindoline, N-benzoylmorpholine, N-benzoylpyrollidine, N-benzoylpiperidine, N-acetyl-5-chloroindoline and N-phenylpyrollidinone.

Definitions

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylaminoand dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

The conversion of colorless, crystalline compounds of the present invention to the colored, amorphous or liquid form can be carried out by applying heat to the compounds, and therefore the compounds are useful in thermal imaging members used in thermal imaging methods. In such thermal imaging methods thermal energy may be applied to the thermal imaging members by any of the techniques known in thermal imaging such as from a thermal print head, a laser, a heated stylus, etc. In another embodiment, the conversion to the liquid form may be effected by applying a solvent for the crystalline solid such as from an ink jet imaging apparatus to at least partially dissolve the crystalline material. In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to the liquid amorphous form to form the image.

The compounds of the invention may be incorporated in any suitable thermal imaging members. Typical suitable thermal imaging members generally comprise a substrate carrying at least one image-forming layer including a compound in the crystalline form, which can be converted, at least partially to a liquid in the amorphous form, the liquid having intrinsically a different color from the crystalline form. The thermal imaging member may be monochrome or multicolor and the temperature at which an image is formed in at least one of the image-forming layers is preferably time independent.

Preferred thermal imaging members according to the invention are those having the structures described in prior co-pending commonly assigned U.S. patent application Ser. No. 09/745,700 filed Dec. 20, 2000, now U.S. Pat. No. 6,537,410 B1 which is hereby incorporated herein by reference in its entirety and made a part of this application.

Other preferred thermal imaging members are those having the structures described in prior, co-pending commonly assigned U.S. patent application Ser. No. 10/151,432 filed May 20, 2002 which is hereby incorporated herein by reference in its entirety and made a part of this application.

Further preferred thermal imaging members are those having the structures described in U.S. Pat. No. 6,054,246 which is hereby incorporated herein by reference in its entirety and made a part of this application.

DETAILED DESCRIPTION OF THE INVENTION

Crystalline complexes formed by more than one compound commonly have properties, including color, that are very different from those of combinations of the same compounds in an amorphous form. In a crystal, each of the molecules is typically held in a single conformation (or, more rarely, in a small number of conformations) by the packing forces of the lattice. Likewise, if a molecule can exist in more than one interconverting isomeric forms, only one of such isomeric forms is commonly present in the crystalline state. In amorphous form or in solution, on the other hand, each molecule may explore its whole conformational and isomeric space, and only a small proportion of the population of individual molecules may at any one time exhibit the particular conformation or isomeric form adopted in the crystal. In the present invention, at least one of the molecules can equilibrate between a colored and a colorless form, both of which are present in the amorphous state but only one, the colorless form, is present in the crystalline state. This potentially colored molecule is hereinafter referred to as the "dye-former".

Two problems commonly occur in designing crystalline, colorless, color-forming compounds having the desired properties. Firstly, it may turn out to be impossible to crystallize the colorless tautomeric form of the dye-former. For example, many of the rhodol-type dye-formers of the present invention cannot be readily crystallized in colorless form. Secondly, the colorless form may be able to be crystallized, but may exhibit a non-ideal melting point. To change the melting point would require a complete redesign of the dye-former, a long and tedious process. The presence of co-crystallizing molecules (referred to herein as complexing agents) together with the dye-former may alleviate either of the problems discussed above. In some cases, the complexing agent facilitates the formation of colorless crystals from the dye former. In other cases, the complexing agent is not necessary for the formation of colorless crystals of the dye former, but is incorporated to allow the tuning of the melting point of the colorless crystals.

The complexing agent should not interfere unduly with the equilibrium between colored and colorless forms of the dye former in the amorphous state. Too strong a complex between the colorless form of the dye former and the complexing agent may lead to a faint color in the amorphous state. An actual chemical reaction, such as a deprotonation, between the complexing agent and the dye former may lead to an inability to form the colorless form of the dye former at all, or may affect the color of the dye formed from the dye former. These requirements limit the basicity of the complexing agent to a narrow range that depends upon the choice of dye former. In the present invention, specific preferred dye formers bear a phenolic group which forms a hydrogen bond with the complexing agent.

Complexes formed between phenolic and amino compounds are well known, and are discussed, for example, in "Equilibria of bisphenol complexation with pyridine in acetonitrile solutions," by Titov, E. V. et al., Zhurnal Obshchei Khimii (1993), 63(8), pp. 1869-71, "Hydrogen-bonding-based thermochromic phenol-amine complexes," by Mizutani, T., et al., J. Phys. Org. Chem. (1998), 11(10), pp. 737-742, and "Hydrogen bond equilibria of phenol-pyridine in cyclohexane, carbon tetrachloride, and benzene solvents," by Spencer, J. N., et al., J. Phys. Chem. (1987), 91(6), pp. 1673-4. Furthermore, U.S. Pat. No. 4,097,288 discloses that certain phenolic or amino compounds readily form co-crystals with hydrogen-bonding acceptors or donors, respectively.

The complexes of the invention are preferably formed by one of the two following procedures.

General Procedure A:

The complexing agent (1.0 or 0.5 equivalents relative to the dye former) was combined with the dye former and the mixture was dissolved in a blend of hot methyl ethyl ketone or ethyl acetate (or other appropriate polar solvent) and cyclohexane or heptane (or other appropriate nonpolar solvent). The complex crystallized from the hot solution during cooling, as colorless or nearly colorless crystals. The crystals were collected by suction filtration and washed with an appropriate blend of the crystallization solvents. This wash was carefully done so as to avoid the precipitation of colored materials on the surface of the crystals. Analysis by $^1$H NMR spectroscopy defined the composition of the complex. Integral ratios of 1:1 and 2:1 of dye former to complexing agent were most commonly observed. As discussed above, the ratio depended both on the structure of the dye and the structure of the complexing agent.

General Procedure B:

The complexing agent (1.0 or 0.5 equivalents relative to dye former) and dye former were combined and ground with an agate mortar and pestle. The resulting intimate mixture was then slurried on the mortar in a small amount of cyclohexane and the grinding was continued. Small amounts of methyl ethyl ketone were then added to facilitate dissolution of the components into the solvent and aid crystal growth. The grinding was continued until a colorless complex was formed. Often the stronger solvent (methyl ethyl ketone) was allowed to slowly evaporate during the grinding process until a critical concentration was achieved. At this point crystallization often proceeded. Once crystallization had occurred additional cyclohexane/methyl ethyl ketone was added and the slurry of crystals was transferred either to a container for further ripening (heating and stirring) or directly collected by suction filtration. The crystals were then carefully washed with an appropriate mixture of cyclohexane/methyl ethyl ketone to avoid precipitating colored dye on the surface of the crystals. Crystals from this procedure could be used to seed crystallizations using General Procedure A.

Specific preferred complexing agents for use in the present invention are shown in Table I below.

TABLE I

| Complexing Agent | |
|---|---|
| I | 1,10-Phenanthroline |
| II | 2,9-Dimethyl-1,10-phenanthroline |
| III | 4,4'-Bipyridyl |
| IV | 1,2-Bis(4-pyridyl)ethylene |
| V | Pyrazine |
| VI | Ethyl picolinate |
| VII | 1-Benzylimidazole |
| VIII | 1-Ethyl-2-methyl-5,6-dichlorobenzimidazole |
| IX | 1-Ethyl-2-phenyl-benzimidazole |
| X | 1-Hexyl-2-phenyl-benzimidazole |
| XI | N-Benzoylmorpholine |
| XII | N-Acetylindoline |
| XIII | N-Propionylindoline |
| XIV | N-Acetyl-5-bromoindoline |

TABLE I-continued

| | Complexing Agent | |
|---|---|---|
| | XV | N,N,N'N'-Tetra-ethylterepthalamide |
| | XVI | N-Phenylpyrollidinone |

Complexes can be formed between fluorescein dye formers and some of the complexing agents shown in Table I. The fluorescein dye formers were prepared according to procedures described in commonly assigned U.S. patent application Ser. No. 10/789,566, filed on even date herewith, the entire disclosure of which is incorporated by reference herein and made part of this application.

Complexes may also be formed between certain rhodol dye formers and some of the complexing agents shown in Table I. The rhodol dyes formers were prepared according to procedures described in commonly assigned U.S. patent application Ser. No. 10/789,276, filed on even date herewith, the entire disclosure of which is incorporated by reference herein and made part of this application.

All specific preferred complexes are of structure represented by formula I as described above, wherein the dye former is shown in its colorless tautomeric form in association with complexing agent A, and in which $R_1$, $R_3$, $R_4$ and $R_7$ are hydrogen, $X_1$ is carbonyl, $X_2$ and $X_3$ are each an oxygen atom and $X_4$ is a carbon atom. The other substituents of formula I are as shown in Table II for fluorescein dye formers and Table III for rhodol dye formers.

The complexes were formed according to procedures A or B as described above (indicated in the column entitled "Proc." in Tables II and III). The ratio shown is the molar ratio between dye former and complexing agent, as estimated by proton NMR spectroscopy, and the melting point reported is the peak of the melting endotherm as measured by differential scanning calorimetry (DSC).

TABLE II

| A | R2 | R5 | R6 | R8–R11 | Proc. | Ratio | m.p. (DSC, °C.) |
|---|---|---|---|---|---|---|---|
| I | H | H | $C_6H_5CH_2O$ | H | A | 1:1 | 201 |
| II | H | H | $C_6H_5CH_2O$ | H | A | 1:1 | 185 |
| III | H | H | $C_6H_5CH_2O$ | H | A | 2:1 | 109 |
| V | H | H | $C_6H_5CH_2O$ | H | A | 1:1 | 125 |
| VI | H | H | $C_6H_5CH_2O$ | H | A | 1:1 | 138 |
| III | $C_2H_5$ | $C_2H_5$ | $C_6H_5CH_2O$ | H | B | 2:1 | 191 |
| III | $C_6H_{13}$ | $C_6H_{13}$ | $CH_3CH_2O$ | H | B | 2:1 | 215 |
| III | $C_2H_5$ | $C_2H_5$ | (3-$CH_3$—$C_6H_4$)$CH_2O$ | H | B | 2:1 | 165 |
| III | $C_6H_5CH_2$ | $C_6H_5CH_2$ | $C_6H_5CH_2O$ | H | B | 2:1 | 198 |

TABLE III

| A | R2 | R5 | R6 | R8–R11 | Proc. | Ratio | m.p. (DSC, °C.) |
|---|---|---|---|---|---|---|---|
| III | Br | H | $C_6H_5N(H)$ | H | A | 2:1 | 170 |
| III | Br | H | $C_6H_5N(C_2H_5)$ | H | B | 2:1 | 210 |
| III | Br | H | $C_6H_5N(C_6H_{13})$ | H | A | 2:1 | 155 |
| III | Br | H | $C_6H_5N(C_{10}H_{21})$ | H | A | 2:1 | 125 |
| III | Br | H | $C_6H_5N(C_{12}H_{25})$ | H | A | 2:1 | 107 |
| III | Br | H | $C_6H_5N(C_{16}H_{33})$ | H | A | 2:1 | 80 |
| III | Br | H | $C_6H_5N(C_6H_5)$ | H | A | 2:1 | 250 |
| III | $C_6H_{13}$ | H | $C_6H_5N(CH_2CH_2CH_2(CH_3)_2)$ | Cl | A | 2:1 | 185 |
| III | $C_6H_{13}$ | H | $C_6H_5N(C_{12}H_{25})$ | Cl | A | 2:1 | 137 |
| III | $C_6H_{13}$ | H | $C_6H_5N(CH_2CH_2(C_2H_5)C_4H_9)$ | Cl | A | 2:1 | 131 |
| III | H | H | N-indolinyl | H | A | 1:1 | 172 |
| II | Br | H | $C_6H_5NH$ | H | A | 1:1 | 244 |
| II | Br | H | $C_6H_5N(C_6H_{13})$ | H | A | 1:1 | 109 |
| II | $C_6H_{13}$ | H | $C_6H_5N(CH_2CH_2CH_2(CH_3)_2)$ | Cl | A | 1:1 | 175 |
| I | $C_6H_{13}$ | H | $C_6H_5N(CH_2CH_2CH_2(CH_3)_2)$ | Cl | A | 1:1 | 110 |
| XI | $C_6H_{13}$ | H | $C_6H_5N(CH_2CH_2CH_2(CH_3)_2)$ | Cl | A | 1:1 | 110 |
| XIII | $C_6H_{13}$ | H | $C_6H_5N(CH_2CH_2CH_2(CH_3)_2)$ | Cl | A | 1:1 | 127 |
| XIV | $C_6H_{13}$ | H | $C_6H_5N(CH_2CH_2CH_2(CH_3)_2)$ | Cl | A | 1:1 | 126 |
| VII | $C_6H_{13}$ | H | $C_6H_5N(CH_2CH_2CH_2(CH_3)_2)$ | Cl | A | 1:1 | 133 |
| VIII | $C_6H_{13}$ | H | $C_6H_5N(CH_2CH_2CH_2(CH_3)_2)$ | Cl | A | 1:1 | 138 |
| XII | $C_6H_{13}$ | H | $C_6H_5N(CH_2CH_2CH_2(CH_3)_2)$ | Cl | A | 1:1 | 139 |
| XV | $C_6H_{13}$ | H | $C_6H_5N(CH_2CH_2CH_2(CH_3)_2)$ | Cl | A | 2:1 | 145 |
| XVI | $C_6H_{13}$ | H | $C_6H_5N(CH_2CH_2CH_2(CH_3)_2)$ | Cl | A | 1:1 | 146 |
| IX | $C_6H_{13}$ | H | $C_6H_5N(CH_2CH_2CH_2(CH_3)_2)$ | Cl | A | 1:1 | 157 |
| X | $C_6H_{13}$ | H | $C_6H_5N(CH_2CH_2CH_2(CH_3)_2)$ | Cl | A | 1:1 | 183 |
| IV | $C_6H_{13}$ | H | $C_6H_5N(CH_2CH_2CH_2(CH_3)_2)$ | Cl | A | 2:1 | 206 |

Although the invention has been described in detail with respect to various preferred embodiments, it is not intended to be limited thereto, but rather those skilled in the art will recognize that variations and modifications are possible which are within the spirit of the invention and the scope of the appended claims.

What is claimed is:

1. An imaging method comprising the steps of:

(a) providing an imaging member comprising an image-forming layer comprising a compound represented by the formula (I)

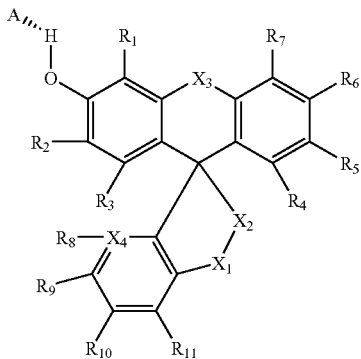

(I)

wherein:

$R_1$, $R_2$, $R_3$, $R_4$, $R_5$, and $R_7$ are each independently selected from the group consisting of: hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_6$ is selected from the group consisting of: halogen, oxygen, substituted oxygen, nitrogen, substituted nitrogen, sulfur and substituted sulfur;

$R_8$, $R_9$, $R_{10}$ and $R_{11}$ are each independently absent or selected from the group consisting of: hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$X_1$ is selected from the group consisting of: carbonyl, methylene, substituted methylene, and sulfonyl;

$X_2$ is selected from the group consisting of: oxygen, nitrogen, or substituted nitrogen;

$X_3$ is selected from the group consisting of: oxygen, sulfur, nitrogen and substituted nitrogen;

$X_4$ is carbon or nitrogen; and

A is a hydrogen-bond accepting group;

said compound being in the crystalline form; and (b) converting at least a portion of said compound to an amorphous form in an imagewise pattern whereby an image is formed.

2. The imaging method as defined in claim 1 wherein step (b) comprises applying an imagewise pattern of thermal energy to said imaging member whereby at least a portion of said compound is converted to an amorphous form and an image is formed.

3. The imaging method as defined in claim 2 wherein said imaging member further includes a substrate and at least a second color-forming layer, said second color-forming layer being capable of forming a color different from that formed by said first color-forming layer.

4. The imaging method as defined in claim 3 wherein said imaging member further includes a third color-forming layer, said third color-forming layer being capable of forming a color different from those formed by said first and second color-forming layers.

5. The imaging method as defined in claim 4 wherein said color-forming layers form magenta, cyan and yellow color, respectively.

* * * * *